United States Patent [19]

Fischer et al.

[11] Patent Number: 4,922,023
[45] Date of Patent: May 1, 1990

[54] PREPARATION OF ALIPHATIC N,N-DIALKYL-SUBSTITUTED AMINO ALCOHOLS

[75] Inventors: Roman Fischer, Mutterstadt; Hans J. Mercker, Mannheim; Herbert Mueller, Frankenthal, all of Fed. Rep. of Germany

[73] Assignee: BASF Aktiengesellschaft, Ludwigshafen, Fed. Rep. of Germany

[21] Appl. No.: 215,736

[22] Filed: Jul. 6, 1988

[30] Foreign Application Priority Data

Jul. 22, 1987 [DE] Fed. Rep. of Germany ....... 3724239

[51] Int. Cl.$^5$ ............................................. C07C 85/06
[52] U.S. Cl. ..................................................... 564/479
[58] Field of Search ......................................... 564/479

[56] References Cited

U.S. PATENT DOCUMENTS

| | | | |
|---|---|---|---|
| 3,270,059 | 8/1966 | Winderl et al. | 260/583 |
| 4,009,124 | 4/1977 | Laurer et al. | 502/346 |
| 4,062,899 | 1/1977 | Laurer et al. | 502/346 |
| 4,442,306 | 11/1984 | Mueller et al. | 502/346 |
| 4,487,967 | 12/1984 | Stogryn et al. | 564/474 |
| 4,680,393 | 7/1987 | Marsella | 544/170 |

FOREIGN PATENT DOCUMENTS

| | | |
|---|---|---|
| 70512 | 7/1984 | European Pat. Off. . |
| 2445303 | 11/1976 | Fed. Rep. of Germany . |
| 2625196 | 4/1977 | Fed. Rep. of Germany . |
| 1585480 | 3/1981 | United Kingdom . |

Primary Examiner—Stanley J. Friedman
Attorney, Agent, or Firm—John H. Shurtleff

[57] ABSTRACT

Preparation of aliphatic N,N-dialkyl-substituted amino alcohols of the general formula I

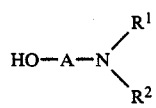

from diols of the general formula II

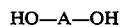

and secondary amines of the general formula III

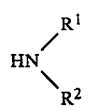

where A is an aliphatic chain of at least 2 carbon atoms and $R^1$ and $R^2$ are alkyl radicals of from 1 to 6 carbon atoms, which may be joined to form a five-membered or six-membered ring—in the liquid phase at elevated temperature and pressure and in the presence of a hydrogenation/dehydrogenation catalyst, hydrogen, and a basic alkali-metal or alkaline-earth-metal compound, where (a) the temperature is from 150° C. to 250° C.; (b) the total pressure is from 40 bar to 250 bar; (c) the hydrogen partial pressure is from 2 bar to 60 bar; (d) the hydrogenation/dehydrogenation catalyst is based on copper; (e) water is present, the mass being from 1% to 20% of the mass of the reaction mixture.

17 Claims, No Drawings

PREPARATION OF ALIPHATIC N,N-DIALKYL-SUBSTITUTED AMINO ALCOHOLS

The present invention relates to an improved process for the preparation of aliphatic N,N-dialkyl-substituted amino alcohols of the general formula I

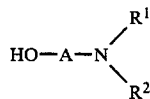  (I)

from diols of the general formula II

HO—A—OH  (II)

and secondary amines of the general formula III

  (III)

where A is an aliphatic chain of at least 2 carbon atoms and $R^1$ and $R^2$ are alkyl radicals of from 1 to 6 carbon atoms, which may be joined to form a five-membered or six-membered ring—in the liquid phase at elevated temperature and pressure and in the presence of a hydrogenation/dehydrogenation catalyst, hydrogen, and a basic alkali-metal or alkaline-earth-metal compound.

The principle of this method, by which tertiary amines are prepared from secondary amines and alcohols under hydrogenating conditions, is well known, but because of the number of side reactions it is necessary to choose special reaction conditions for each pair of reactants if satisfactory results are to be achieved.

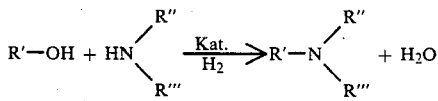

In DE-C 26 25 196 it is recommended that water should be removed continually when a monohydric or polyhydric alcohol reacts with a secondary amine in the liquid phase in the presence of a hydrogenation/dehydrogenation catalyst and a basic alkali-metal or alkaline-earth-metal compound. Although this procedure has proved useful in general, it is not satisfactory for the preparation of amino alcohols of the general formula I because of insufficient selectivity.

The process given in EP-B 70 512, which differs from that given in DE-C 26 25 196 in that the catalyst used is that formed from copper formate under the conditions of the reaction, is similarly unsatisfactory. In this case too conversion of diols to amino alcohols does not succeed as well as the conversion of monohydric alcohols to tertiary amines.

DE-A 28 24 908 describes the preparation of bis-tertiary diamines from diols like the diol II and secondary amines in the liquid phase and in the presence of hydrogen and (inter alia) copper catalysts. The reaction is carried out in two stages, the water formed being removed. N,N-Disubstituted amino alcohols like the amino alcohol I are formed as side products.

The object of the present invention is to make N,N-dialkyl-substituted amino alcohols of the general formula I accessible in higher yield and selectivity. These compounds are especially important as intermediates.

We have found that this object is attained by a process in which aliphatic N,N-dialkyl-substituted amino alcohols of the general formula I

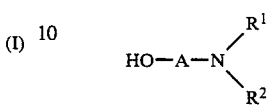  (I)

are prepared from diols of the general formula II

HO—A—OH  (II)

and secondary amines of the general formula III

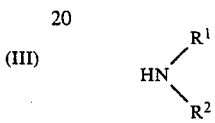  (III)

where A is an aliphatic chain of at least 2 carbon atoms and $R^1$ and $R^2$ are alkyl radicals of from 1 to 6 carbon atoms, which may be joined to form a five-membered or six-membered ring—in the liquid phase at elevated temperature and pressure and in the presence of a hydrogenation/dehydrogenation catalyst, hydrogen, and a basic alkali-metal or alkaline-earth-metal compound if (a) the temperature is from 150° C. to 250° C.;
(b) the total pressure is from 40 bar to 250 bar;
(c) the hydrogen partial pressure is from 2 bar to 60 bar;
(d) the hydrogenation/dehydrogenation catalyst is based on copper; (e) water is present, the mass being from 1% to 20% of the mass of the reaction mixture.

Suitable diols of general formula II are in particular bis-primary alkanediols where A is an unbranched alpha,omega-alkylene radical of from 2 to 8 carbon atoms; they include, for instance, ethylene glycol, 1,3-propanediol, 1,4-butanediol, 1,5-pentanediol, and 1,6-hexanediol. Some ether diols are also of special importance; these are typified by diethylene glycol (3-oxa-1,5-pentanediol), triethylene glycol (3,6-dioxa-1,8-octanediol), and di(1,3-propanediol) (4-oxa-1,7-heptanediol).

In general diols with primary hydroxyl groups are preferred: diols with secondary or tertiary hydroxyl groups are of subsidiary importance. The chain to which the hydroxyl groups are attached is preferably a linear alkylene radical, but it can include ether oxygen atoms and it can carry methyl, ethyl, methoxy, or ethoxy as substituents. The total number of carbon atoms in A is preferably not more than 12, in particular up to 6.

The preferred secondary amines are those with up to 6 carbon atoms, for example methylpropylamine, methylbutylamine, ethylbutylamine, dipropylamine, diisopropylamine, and, above all, dimethylamine, diethylamine, and methylethylamine. The alkyl groups can also be joined to form a five-membered or six-membered heterocyclic ring, as in amines such as pyrrolidine, pipridine, and their methyl homologues.

The ratio of the amount of diol to the amount of amine is preferably at least 1:1, particularly good results being obtained with ratios of from 2:1 to 5:1. There is generally no economic advantage in making the ratio greater than 10:1.

Hydrogenation/dehydrogenation catalysts based on copper are those whose catalytic activity is ascribable mainly to copper and whose active mass consists of at least 80% copper.

The copper can be in the form of powder, turnings, or the Raney metal, but is best prepared by reduction of a copper compound such as copper acetate, copper propionate, or copper oxide, in situ if required. For instance, very good results are obtained with catalyst formed from copper formate under the conditions of the reaction, as described in EP-B 70 512.

Catalysts prepared as described in DE-A 24 45 303 are also outstandingly suitable. An aqueous solution of a copper salt and an aluminum salt, for instance copper nitrate and aluminum nitrate in the molar ratio of from about 0.2:1 to 1:1, is treated with an alkali-metal carbonate and the mixed copper and aluminum basic carbonates that precipitate are formed into round pellets or rods and dried. Under the conditions of the reaction these catalyst pellets are converted into porous structures of aluminum oxides and hydrated oxides coated with a large area of metallic copper.

It is also possible to prepare supported copper catalyst by soaking materials such as pumice, diatomaceous earth, silica gel, or alumina in a solution of a copper salt and reducing.

It is of course always possible to activate the catalyst, that is to say, to reduce the copper compound to metallic copper, by treatment with hydrogen or reducing agents such as alcohols apart from the novel reaction process.

For batchwise operation the catalyst is preferably employed as a fine suspension, whereas a fixed bed is to be recommended for continuous operation.

The ratio of the mass of copper catalyst to the mass of the reactants is preferably from 10 g/kg to 150 g/kg, especially from 20 g/kg to 70 g/kg, for batchwise operation. For continuous operation the mass of copper divided by the throughput of reactants is preferably from 100 g/(kg.h$^{-1}$) to 500 g/(kg.h$^{-1}$), especially from 200 g/(kg.h$^{-1}$) to 400 g/(kg.h$^{-1}$).

The catalyst can contain subsidiary proportions of other metals apart from the copper, for example cobalt and nickel.

The basic alkali-metal or alkaline-earth-metal compound (mineral base), whose presence suppresses undesirable rearrangements involving alkyl groups, can be one of any number of such compounds, but economic considerations suggest the use of sodium or potassium hydroxide, sodium carbonate, calcium oxide, or calcium hydroxide. The important thing is that the mineral base should provide hydroxide ions with water, and for this reason it is preferably introduced in aqueous solution. The basic compound should be present in the reaction mixture in its free form, not, for instance, as a basic component of the copper catalyst. The amount of basic compound is preferably such that the amount of hydroxide ion per unit mass of reactant mixture is from 5 mmol/kg to 200 mmol/kg, especially from 20 mmol/kg to 100 mmol/kg.

The employment of water is the feature of the novel combination to which special importance must be attached, since it considerably increases the selectivity of the reaction with respect to the amino alcohols I. Since in any case water is formed in the course of the reaction, it is sufficient if this water is simply left in the reaction mixture and not removed as usually recommended. At the start of the reaction some water does have to be provided, but this is best done by introducing the basic alkali-metal or alkaline-earth metal compound as an aqueous solution, as mentioned above. In principle it is not even essential to provide water at the start of the reaction, since there is enough present after about 10% conversion. Within the defined range, from 1% to 20% of the mass of the reaction mixture, the preferred mass fraction of water is from 5% to 10%. Above 20% the reaction slows too much and is not so attractive for industrial purposes.

Within the temperature range of from 150° C. to 250° C. the best results are usually obtained at temperatures between 170° C. and 230° C.

The total pressure is not critical: it can be from 40 bar to 250 bar, although the reaction is generally carried out under a total pressure of from 50 bar to 150 bar. The hydrogen partial pressure, which can be from 2 bar to 60 bar, should be not more than from 5% to 80% of the total pressure.

The process has no peculiarities with respect to apparatus or processing technology. In batchwise operation it is generally advisable to place the diol II, in which the catalyst is suspended, the aqueous solution or suspension of the mineral base, and some water in the vessel and to add the amine III gradually as the reaction proceeds, the temperature and pressure being maintained at the required values. In continuous operation the diol and the amine are passed over the copper fixed-bed catalyst in the chosen proportion; the mineral base and water can be dissolved or suspended in either component or both components.

In both batchwise and continuous operation it is not difficult to arrange that the amine III is completely or almost completely converted, by choosing appropriate residence times and other conditions. This makes subsequent distillation of the reaction mixture particularly easy. Unreacted starting material and mineral base can be recovered and reused in further charges or recirculated through the reactor.

The novel process permits simple, ecomonic, and selective preparation of amino alcohols of the general formula I in high yields. It is a particular advantage that very small proportions of substances with high boiling temperatures are formed, so that subsequent treatment of the reaction mixtures causes correspondingly little difficulty.

These amino alcohols serve as basic catalysts for the preparation of polyurethanes and are intermediates for the preparation of dyes, drugs, and crop-protection agents. The process is of particular importance for the conversion of the appropriate diols II and secondary amines III to N,N-(dimethylamino)-2-ethanol
N,N-(diethylamino)-2-ethanol
N,N-(dimethylamino)-4-butanol
N,N-(dimethylamino)-5-pentanol
N,N-(dimethylamino)-6-hexanol
N,N-(dimethylamino)-3-oxa-5-pentanol
N,N-(diethylamino)-4-butanol

EXAMPLE 1

Preparation of N,N-(dimethylamino)-3-oxa-5-pentanol

A vertical tube reactor 125 cm high and 3.2 cm in diameter was packed with 700 ml of copper catalyst prepared as described below. A mixture of 318 g of diethylene glycol (3mol), 3 g of water, 68 g of dimethylamine (1.5 mol), and 0.3 g of 50% sodium hydroxide solution was passed through the reactor each hour at a temperature of 210° C. and a total pressure of 120 bar, the hydrogen partial pressure being 50 bar. The throughput of water rose to about 19 g/h (about 5% of the mixture) in the course of the reaction.

Subsequent distillation of the reaction mixture gave a 67% yield (based on the amount of dimethylamine) of N,N-(dimethylamino)-3-oxa-5-pentanol; there was also a 2% yield of N,N,N'-tetramethyl-3-oxa-1,5-pentanediamine and a 2% yield of N-methylmorpholine. Conversion of dimethylamine was 71%. The mass fraction of high-boiling substances in the reaction mixture was less than 0.5%.

The catalyst was prepared in accordance with Example 1 of DE-B 24 25 303. Sodium hydrogen carbonate was added to an aqueous solution of copper nitrate and aluminum nitrate in the molar ratio 1:1.2 and the mixed carbonates were formed into cylinders 3 mm long and 3 mm in diameter and dried. The cylindrical pellets were packed in the tube reactor and reduced to the form containing active metallic copper by passing 0.01% methanolic sodium methoxide at the rate of 300 ml/h at a temperature of from 180° C. to 200° C. under hydrogen at a pressure of 50 bar.

EXAMPLE 2

Preparation of N,N-(dimethylamino)-4-butanol

A mixture of 270 g of 1,4-butanediol (3 mol), 68 g of dimethylamine (1.5 mol), and 0.027 g of 30% potassium hydroxide solution was passed through the reactor each hour under the conditions given in Example 1. The mass fraction of water rose to about 6% in the course of the reaction.

Gas chromatographic analysis of the reaction mixture showed that the yield of N,N-(dimethylamino)-4-butanol was 65% and that 70% of the dimethylamine was converted. The yields of the side products N,N,N',N'-tetramethyl-1,4-diaminobutane and N-methylpyrrolidine were 3% and 1% respectively. The mass fraction of high-boiling substances in the mixture was less than 0.5%.

EXAMPLE 3

Preparation of N,N(diethylamino)-2-ethanol

A mixture of 186 g of ethylene glycol (3 mol), 117 g of diethylamine (1.6 mol), and 0.15 g of 50% sodium hydroxide solution was passed through a reactor as in Example 1 each hour at a temperature of 200° C. and a total pressure of 150 bar, the hydrogen partial pressure being 45 bar. The mass fraction of water rose to 6% in the course of the reaction.

Subsequent distillation of the reaction mixture gave a 50% yield of N,N-(diethylamino)-2-ethanol; there was also a 4% yield of N,N,N',N'-tetraethylethylenediamine. Conversion of diethylamine was 54%. The mass fraction of high-boiling side products in the mixture was about 4%.

EXAMPLE 4

Preparation of N,N-(dimethylamino)-3-oxa-5-pentanol

A mixture of 731 g of diethylene glycol (about 7 mol), 156 g of dimethylamine (3.5 mol), 5.5 g of calcium hydroxide, and 55 g of metallic copper catalyst was reacted over a period of 6 h at a temperature of 210° C. and a pressure of from 60 bar to 80 bar, the hydrogen partial pressure being 40 bar. The mass fraction of water rose to about 6% in the course of the reaction.

Subsequent distillation of the reaction mixture gave a 68% yield of the required amino alcohol; there was also a 9% yield of the substituted diamine and an 11% yield of 4-methylmorpholine. Conversion of dimethylamine was 89%. The mass fraction of high-boiling substances in the mixture was about 0.3%.

If during the course of the reaction the water formed was largely removed by gas circulation and partial condensation the yield of the required product dropped to 25%.

The catalyst was prepared beforehand by reducing copper formate with hydrogen at 200° C. in lauryl alcohol saturated with dimethylamine.

We claim:

1. In a process for the preparation of an aliphatic N,N-dialkyl-substituted amino alcohol of the formula

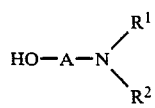
(I)

from a diol of the formula $$HO-A-OH \quad (II)$$

and a secondary amine of the formula

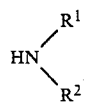
(III)

where A is an aliphatic chain of at least 2 up to 12 carbon atoms and $R^1$ and $R^2$ are alkyl of from 1 to 6 carbon atoms, which may be joined to form a five-membered or six-membered ring, by reaction of said diol and said amine in the liquid phase with hydrogen at elevated temperature and pressure and in the presence of a hydrogenation/dehydrogenation catalyst and a basic alkali-metal or alkaline-earth-metal compound, the improvement which comprises:

carrying out said reaction at a temperature of from 150° C. to 250° C. and at a total pressure of from 40 bar to 250 bar with the hydrogen partial pressure being from 2 bar to 60 bar while using a hydrogenation/dehydrogenation catalyst which is based on copper; and maintaining a mass of water present during the reaction such that the mass of said water is from 1% to 20% of the mass of the reaction mixture.

2. A process as claimed in claim 1 applied to a reaction with an unbranched alpha,omega-alkanediol of from 2 to 8 carbon atoms, up to 2 of which can be replaced by ether oxygen.

3. A process as claimed in claim 1 applied to a reaction with dimethylamine or diethylamine.

4. A process as claimed in claim 1 wherein the copper catalyst is prepared by the reduction of mixed copper and aluminum carbonates precipitated by an alkali-metal carbonate from an aqueous solution of copper and aluminum salts.

5. A process as claimed in claim 1 wherein the copper catalyst is prepared by the reduction of copper formate.

6. A process as claimed in claim 2 wherein the diol reactant is an unbranched alpha, omega-alkanediol of from 2 to 6 carbon atoms.

7. A process as claimed in claim 2 wherein the diol reactant is selected from the group consisting of diethylene glycol, triethylene glycol and di-(1,3-propanediol).

8. A process as claimed in claim 2 wherein the diol reactant is ethylene glycol.

9. A process as claimed in claim 2 wherein the diol reactant is diethylene glycol.

10. A process as claimed in claim 2 wherein the diol reactant is 1,4-butanediol.

11. A process as claimed in claim 1 wherein the mass of said water is from about 5 to 10% of the mass of the reaction mixture.

12. A process as claimed in claim 1 wherein the ratio of the amount of diol to the amount of amine is at least 1:1 up to about 10:1.

13. A process as claimed in claim 1 wherein the ratio of the amount of diol to the amount of amine is about 2:1 to 5:1.

14. A process as claimed in claim 13 wherein the diol reactant is selected from the group consisting of diethylene glycol, triethylene glycol and di-(1,3-propanediol).

15. A process as claimed in claim 13 wherein the diol reactant is ethylene glycol.

16. A process as claimed in claim 13 wherein the diol reactant is diethylene glycol.

17. A process as claimed in claim 13 wherein the diol reactant is 1,4-butanediol.

* * * * *